United States Patent
Dixon et al.

(10) Patent No.: US 11,253,453 B2
(45) Date of Patent: Feb. 22, 2022

(54) REDUCING COLOUR LOSS FROM A DYED MATERIAL BY USING AN AMINE SALT OF A CARBOXYLIC ACID

(71) Applicant: INNOSPEC LIMITED, Ellesmere Port (GB)

(72) Inventors: Nicholas John Dixon, Chester (GB); Matthew Robert Giles, Chester (GB); Kimberley Elizabeth Griffiths, Denbighshire (GB); Tony Gough, Chester (GB); Ian Malcolm McRobbie, Chester (GB)

(73) Assignee: Innospec Limited, Cheshire (GB)

( * ) Notice: Subject to any disclaimer, the term of this patent is extended or adjusted under 35 U.S.C. 154(b) by 0 days.

(21) Appl. No.: 16/338,001

(22) PCT Filed: Sep. 29, 2017

(86) PCT No.: PCT/GB2017/052920
§ 371 (c)(1),
(2) Date: Mar. 29, 2019

(87) PCT Pub. No.: WO2018/060720
PCT Pub. Date: Apr. 5, 2018

(65) Prior Publication Data
US 2019/0269590 A1 Sep. 5, 2019

(30) Foreign Application Priority Data
Sep. 30, 2016 (GB) ..................... 1616657

(51) Int. Cl.
*A61K 8/33* (2006.01)
*A61K 8/36* (2006.01)
*A61K 8/49* (2006.01)
*A61Q 5/00* (2006.01)
*D06P 3/14* (2006.01)
*D06P 5/06* (2006.01)
*D06P 1/649* (2006.01)
*A61Q 5/10* (2006.01)
*A61K 8/41* (2006.01)

(52) U.S. Cl.
CPC .............. *A61K 8/361* (2013.01); *A61K 8/33* (2013.01); *A61K 8/36* (2013.01); *A61K 8/416* (2013.01); *A61K 8/4913* (2013.01); *A61Q 5/004* (2013.01); *A61Q 5/10* (2013.01); *D06P 1/6496* (2013.01); *D06P 3/148* (2013.01); *D06P 5/06* (2013.01); *A61K 2800/42* (2013.01)

(58) Field of Classification Search
None
See application file for complete search history.

(56) References Cited

U.S. PATENT DOCUMENTS

| | | | |
|---|---|---|---|
| 3,871,817 A | 3/1975 | Harper, Jr. et al. | |
| 3,944,598 A * | 3/1976 | Paustian | C07C 51/54 562/480 |
| 4,010,872 A | 3/1977 | Lozano et al. | |
| 5,573,553 A | 11/1996 | McBride et al. | |
| 2004/0187226 A1 | 9/2004 | Muerner et al. | |
| 2008/0229521 A1 | 9/2008 | Lalleman | |
| 2009/0049623 A1* | 2/2009 | Brown | A61Q 5/02 8/442 |
| 2010/0278767 A1 | 11/2010 | Hoffkes et al. | |
| 2011/0028376 A1 | 2/2011 | Harrison et al. | |
| 2015/0034117 A1 | 2/2015 | Pressly et al. | |
| 2015/0034119 A1 | 2/2015 | Pressly et al. | |
| 2019/0091120 A1 | 3/2019 | Gough et al. | |
| 2019/0091121 A1 | 3/2019 | Dixon et al. | |
| 2019/0269591 A1 | 9/2019 | Dixon et al. | |

FOREIGN PATENT DOCUMENTS

| | | | | |
|---|---|---|---|---|
| EP | 0687721 A2 | 12/1995 | | |
| GB | 981825 A | 1/1965 | | |
| JP | 4112820 A | 4/1992 | | |
| JP | H04338319 A | 10/1996 | | |
| JP | 2004210700 A | 7/2004 | | |
| JP | 2014511420 A | 6/2014 | | |
| JP | 2014218572 A1 | 12/2017 | | |
| WO | 2002030373 A2 | 4/2002 | | |
| WO | WO 2014/123805 | * | 8/2014 | ............... A61K 8/49 |
| WO | 2015038601 A1 | 3/2015 | | |
| WO | 2018060719 A1 | 5/2018 | | |
| WO | 2018060720 A1 | 5/2018 | | |

OTHER PUBLICATIONS

International Preliminary Report on Patentability dated Apr. 11, 2019 for International Application No. PCT/GB2017/052920.
http://www.gnod.com "Shampoo".
http://www.gnpd.com "Sulfate-Free Color Lock".
Orsavova, Jana et al. "Fatty Acids Composition of Vegetable Oils and Its Contribution to Dietary Energy Intake and Dependence of Cardiovascular Mortality on Dietary Intake of Fatty Acids" Int. J. Mol. Sci. 2015, 16, 12871-12890; DOI: 10.3390/IJMS160612871.
Database GNPD [Online] Mintel; Jul. 31, 2015; Anonymous, "Super Special Shampoo" XP002775650, retrieved from www.gnpd.com.
Search Report and Written Opinion dated Mar. 21, 2018 in PCT/GB2017/052920.
Verhovnik et al.; Silsoft A-553 Conditioning Agent and SILSOFT A-454 Colour Retaining Conditioning Agent: New Dimethicone Conditions for Hair Care, EURO-COSME, Heidelberg DE, No. 3, Jan. 1, 2002.
Search Report dated Jun. 16, 2017 in GB1616657.1.

* cited by examiner

Primary Examiner — Craig D Ricci
(74) Attorney, Agent, or Firm — Carlos A. Fisher; Stout, Uxa & Buyan, LLP

(57) ABSTRACT

A method of combatting colour loss from a dyed material, the method comprising contacting the material with a composition comprising an amine salt of a carboxylic acid wherein the carboxylic acid has 4 to 10 carbon atoms.

15 Claims, No Drawings

REDUCING COLOUR LOSS FROM A DYED MATERIAL BY USING AN AMINE SALT OF A CARBOXYLIC ACID

CROSS-REFERENCE TO RELATED APPLICATIONS

This application is a U.S. national stage application under 35 U.S.C. 371 of co-pending International Application No. PCT/GB2017/052920, filed on Sep. 29, 2017, and entitled REDUCING COLOUR LOSS FROM A DYED MATERIAL BY USING AN AMINE SALT OF A CARBOXYLIC ACID, which in turn claims priority to and benefit of Great Britain Patent Application No. 1616657.1, filed on Sep. 30, 2016, which are incorporated by reference herein in theft entirety for all purposes.

The present invention relates to a method of treating a dyed material, to compositions for use in such methods and to uses relating thereto. In particular the present invention relates to a method of treating a dyed keratinous material, especially hair. The method is especially useful for reducing, inhibiting or preventing the loss of colour from dyed materials, especially dyed hair.

Procedures for dyeing materials, especially hair and other keratinous materials, have been in existence for many years. However the dyed materials lose colour intensity and vibrancy after dyeing. One cause of this loss of colour is believed to be leaching of dye molecules from the materials when in contact with water or other solvents which can dissolve/solubilise the dyes and cause them to diffuse out of the material. This colour loss can thus occur during processes such as washing of the material (or shampooing in the case of hair) or during other processes where the material comes into contact with water or other solvents that can leach dyes from the material. The problem is greater in the case of small dye molecules as these are more mobile and can thus be leached from the material at a faster rate than larger dye molecules. As a result, repeated washing of materials can lead to colour loss over time. This can also cause a colour shift, for example whereby one or more dye compounds present in a mixture used to colour a material are leached from the material to a greater extent than the others during washing.

For textile materials and fabrics colour loss can occur during washing of the material, either in a hand washing process or in an automatic washing machine.

One effective means by which colour loss can be prevented or inhibited is by treatment with formaldehyde. However formaldehyde is a suspected carcinogen and thus its use in cosmetic compositions is strictly regulated and highly undesirable. There have been numerous attempts to provide alternative means for combatting colour loss from hair. However to date none of these have been completely satisfactory and there therefore exists a need to develop further improved strategies.

It is an aim of the present invention to provide means for reducing, inhibiting or preventing colour loss from dyed materials.

According to a first aspect of the present invention there is provided a method of combating colour loss from a dyed material, the method comprising contacting the material with a composition comprising an amine salt of a carboxylic acid wherein the carboxylic acid has 4 to 10 carbon atoms.

The present invention relates to a method of combating colour loss from a dyed material. The method may involve treating a material which has been dyed and/or it may involve treating a material which is going to be dyed and/or it may involve treating a material as part of the dyeing process.

Preferably the method is a method of combatting colour loss from a material that has been dyed.

Suitably in such embodiments the method is not part of the dyeing process. Rather it is a separate unrelated process that may be carried out any time after, and much later than the dyeing process.

The method may be used to treat any material which has been dyed/is being dyed by any means.

In some embodiments the method of the present invention may be used to combat colour loss from a dyed textile material. In such embodiments the dyed textile material suitably comprises wool and preferably comprises wool as a major proportion thereof.

In preferred embodiments the material is a keratinous material. More preferably the material comprises keratinous fibres. Preferably the material is hair. The hair may be human or animal hair. In especially preferred embodiments the method of the present invention is a method treating human hair. Most preferably it is a method of treating human hair growing on the head.

However it will be appreciated that the method of the present invention can also be used to combat colour loss from hair that is not still growing (i.e. has been removed), such as a wig or animal hair, for example wool.

In especially preferred embodiments the present invention relates to a method of treating dyed hair to combat colour loss. The method may be used to combat colour loss, from hair that has been dyed by any means. For example the invention may be used to combat colour loss from hair that has been dyed using direct dyes. The types of compounds that are classified as direct dyes for hair will be known to the person skilled in the art and include nitrophenylenediamine compounds (eg, 2-nitro-o-phenylenediamine, HC Yellow 10, HC Red 14, N,N'-bis-(2-hydroxyethyl)-2-nitro-p-phenylenediamine, HC Violet 2 and HC Blue 2); nitroaminophenol compounds (eg, HC Yellow 4, 2-amino-3-nitrophenol, HC Orange 3, 4-hydroxypropylamino-3-nitrophenol and 3-nitro-p-hydroxyethylaminophenol); and anthraquinone compounds (eg, Disperse Red 11, Disperse Violet 4, Disperse Blue 3 and HC Blue 14). However the method of the present invention is particularly effective at preventing colour loss from hair that has been dyed using oxidative dyes.

Oxidative dyeing of hair is commonly used for permanent, semi-permanent or demi-permanent colouration of the hair. It involves treatment of the hair with small substituted aromatic compounds (for example phenols, naphthols, phenylene diamines and amino phenols (known as intermediates)) which are oxidised to produce the active dye molecules in situ. Hair colouring methods of this type will be very well known to persons skilled in the art.

The method of the present invention involves contacting the material, preferably hair, with a composition comprising a salt of an amine and a carboxylic acid having 4 to 10 carbon atoms.

In some embodiments the method of the first aspect of the present invention is not a method of dyeing a material, such as hair but rather it is a method of treating a dyed material.

In some embodiments the method may be carried out any time prior to, during or shortly after dyeing the material, as part of the dyeing process.

In embodiments in which the method of the first aspect is carried out any time prior to, during or shortly after dyeing the hair, the present invention may further provide an improved hair colouring method. By shortly before or after dyeing we mean preferably within 2 hours, more preferably within 1 hour, suitably within 30 minutes.

According to a second aspect of the present invention there is provided a method of colouring hair, the method comprising:
(a) contacting the hair with a colouring composition; and
(b) contacting the hair with a composition comprising an amine salt of a carboxylic acid wherein the carboxylic acid has 4 to 10 carbon atoms.

The present invention relates to a method of colouring hair using a colouring composition. This may also be referred to herein as a method of dyeing hair using a dyeing composition.

The method of the second aspect is a method of colouring hair. By this we mean to include colouring human hair or colouring animal hair, including wool. Preferably the method of the second aspect is a method of colouring human hair. More preferably it is a method of colouring human hair growing on the head.

Steps (a) and (b) may be carried out separately in any order or they may be carried out simultaneously.

In some embodiments step (b) is carried out before step (a) and thus the method involves a step of pre-treating hair with a composition comprising amine salt of a carboxylic acid wherein the carboxylic atom has 4 to 10 carbon atoms prior to dyeing.

In some embodiments steps (a) and (b) may be carried out simultaneously and the method involves contacting the hair with a colouring composition comprising the amine salt of a carboxylic acid wherein the carboxylic acid has 4 to 10 carbon atoms.

In some preferred embodiments step (b) is carried out after step (a). Suitably the hair is rinsed and optionally dried between step (a) and step (b).

Step (a) may involve contacting the hair with any suitable colouring composition. Such compositions will be known to the person skilled in the art.

In some preferred embodiments step (a) may involve forming the colouring composition in the hair in situ by applying dye precursor compounds and an oxidising composition (a developer) in an oxidative dyeing method.

In some embodiments step (a) may involve contacting the hair with a colouring composition comprising one or more direct dyes.

In some embodiments the method of the first aspect of the present invention is not carried out as part of the dyeing process and the composition contacted with the hair may be in the form of a shampoo composition, a conditioning composition, a hair styling composition, a hair permanent waving composition, a hair permanent straightening composition, a hair relaxing composition or a subsequent hair colouring/hair dyeing composition.

Compositions which perform multiple functions, for example combined shampoo and conditioning compositions are also within the scope of the invention.

According to a third aspect of the present invention there is provided a hair care composition comprising an amine salt of a carboxylic acid wherein the carboxylic acid has 4 to 10 carbon atoms.

Preferred features of the first, second and third aspects of the invention will now be described. Any feature may apply to any other aspect as appropriate. Thus the method of the first aspect and the method of the second aspect may suitably involve contacting the hair with a composition comprising an amine salt of a carboxylic acid as defined in relation to the third aspect.

The composition of the third aspect of the present invention comprises a salt of an amine and a carboxylic acid having 4 to 10 carbon atoms.

Some preferred carboxylic acids have from 5 to 9 carbon atoms, for example 6 to 8 carbon atoms.

Suitable carboxylic acids include monocarboxylic acids, dicarboxylic acids and polycarboxylic acids.

Monocarboxylic acids are preferred.

In preferred embodiments the carboxylic acid includes a hydrocarbon chain. This is suitably a chain with a carbon backbone. However compounds in which the carbon backbone is interrupted by one or more heteroatoms are also within the scope of the invention. For example the carbon backbone may be interrupted by one or more oxygen, sulphur or nitrogen molecules and thus the carboxylic acid may include an ether, a thioether, an amine or a disulfide moiety.

The carboxylic acid may be predominantly aliphatic or predominantly aromatic in nature. Preferably the carboxylic acid is aliphatic. However it may include one or more double bonds and/or a cyclic group. It may be straight-chain or branched.

In some especially preferred embodiments the salt is of a carboxylic acid of formula RCOOH, wherein R is an optionally substituted hydrocarbyl group having 3 to 9 carbon atoms.

R may be an optionally substituted alkyl, alkenyl or aryl group having 3 to 9 carbon atoms, preferably 4 to 8 carbon atoms, more preferably 5 to 7 carbon atoms.

Preferably R is an optionally substituted alkyl or alkenyl group having 3 to 9, preferably 4 to 8, suitably 5 to 7 carbon atoms.

R may be substituted with one or more substituents selected from keto, hydroxyl, halo, carboxy, acyl, nitro, amino, mercapto, alkoxy, sulfoxy, ester, nitrile, isonitrile or amide. The carbon backbone may be interrupted by one or more heteroatoms, for example one or more oxygen, nitrogen or sulfur atoms.

Preferably R is a straight chain alkyl group.

In some preferred embodiments R is an unsubstituted alkyl group having 3 to 9, preferably 4 to 8, more preferably 5 to 7 carbon atoms.

Suitably R is selected from propyl, butyl, pentyl, hexyl, heptyl, cetyl, nonyl, including isomers and mixtures thereof.

Preferably R is selected from n-pentyl and n-heptyl.

Most preferably R is n-heptyl.

The present invention relates to the salt of a carboxylic acid and an amine.

Any suitable amine may be used to form the salt. Suitable amines include ammonia, and primary, secondary and tertiary amines.

In some embodiments the amine is ammonia.

In some preferred embodiments the amine is an alkylamino and/or hydroxyalkyl amino compound of formula $R^1R^2R^3N$, wherein each of $R^1$, $R^2$ and $R^3$ is hydrogen or an alkyl group or a hydroxyalkyl group. Each of $R^1$, $R^2$ and $R^3$ may be the same or different. Suitably each of $R^1$, $R^2$ and $R^3$ is independently selected from hydrogen and an alkyl or hydroxyalkyl group having 1 to 6 carbon atoms, for example 1 to 4 carbon atoms. Each of $R^1$, $R^2$ and $R^3$ may be independently selected from hydrogen, methyl, ethyl, propyl, butyl, pentyl, hexyl, hydroxymethyl, hydroxyethyl, hydroxypropyl, hydroxybutyl, hydroxypentyl, hydroxyhexyl and isomers thereof. The amine may be an alkylamine, a hydroxyalkylamine, a dialkylamine, a hydroxyalkyl alkyl amine, a dihydroxyalkylamine, a trialkylamine, a dialkylhydroxyalkylamine, a dihydroxyalkylalkylamine or a trihydroxyalkylamine. There are many different compounds of this type and these will be known to the person skilled in the art. In some embodiments the amine is a cyclic amine.

In some embodiments the amine is a primary amine. Suitable primary amines include methylamine, ethylamine, propylamine, butylamine, pentylamine, hexylamine, 2-aminobutanol, ethanolamine, cyclohexylamine, aminopropanediol, isopropanolamine, mixed isopropanolamines, tromethamine and benzyl amine.

Preferably the amine is a secondary amine or a tertiary amine.

Suitable secondary amine compounds for use herein include dimethylamine, N,N-methylethylamine, N,N-methylpropylamine, N,N-methylbutylamine, diethylamine, N,N-ethylpropylamine, N,N-ethylbutylamine, dipropylamine, N,N-propylbutylamine, dibutylamine, N,N-butylmethylamine, N,N-butylethylamine, N,N-butylpropylamine, N,N-methylmethanolamine, N,N-methylethanolamine, diethanolamine, N,N-methylpropanolamine, dipropanolamine, N,N-methylbutanolamine, dibutanolamine, N,N-ethylmethanolamine, N,N-ethylethanolamine, N,N-ethylpropanolamine, N,N-ethylbutanolamine, N,N-propylmethanolamine, N,N-propylethanolamine, N,N-propylpropanolamine, N,N-propylbutanolamine, N,N-butylmethanolamine, N,N-butylethanolamine, N,N-butylpropanolamine, N,N-butylbutanolamine, 2(2-aminoethoxy)ethanol, aminoethyl propanediol, aminomethyl propanediol, aminoethyl propanol, diisopropylamine, diisopropanolamine, morpholine and mixtures and isomers thereof.

Some preferred tertiary amine compounds for use herein include trimethylamine, N,N-dimethylethylamine, N,N-dimethylpropylamine, N,N-dimethylbutylamine, triethylamine, N,N-diethylmethylamine, N,N-diethylpropylamine, N,N-diethylbutylamine, tripropylamine, N,N-dipropylmethylamine, N,N-dipropylethylamine, N,N-dipropylbutylamine, tributylamine, N,N-dibutylmethylamine, N,N-dibutylethylamine, N,N-dibutylpropylamine, N,N-dimethylmethanolamine, methyldimethanolamine, N,N-dimethylethanolamine, methyldiethanolamine, N,N-dimethylpropanolamine, methyldipropanolamine, N,N-dimethylbutanolamine, methyldibutanolamine, N,N-diethylmethanolamine, ethyldimethanolamine, N,N-diethylethanolamine, ethyldiethanolamine, N,N-diethylpropanolamine, ethyldipropanolamine, N,N-diethylbutanolamine, ethyldibutanolamine, N,N-dipropylmethanolamine, propyldimethanolamine, N,N-dipropylethanolamine, propyldiethanolamine, N,N-dipropylpropanolamine, propyldipropanolamine, N,N-dipropylbutanolamine, propyldibutanolamine, N,N-dibutylmethanolamine, butyldimethanolamine, N,N-dibutylethanolamine, butyldiethanolamine, N,N-dibutylpropanolamine, butyldipropanolamine, N,N-dibutylbutanolamine, butyldibutanolamine, trimethanolamine, triethanolamine, tripropanolamine, tributanolamine, diethylhexylamine, dimethyltolylamine, bis-hydroxyethyl tromethamine, diethylethanolamine, dimethylamino methylpropanol, dimethyl isopropanolamine, dimethyl MEA, hydroxyethyl methyl tolyl amine, triisopropanolamine, bis-tris and mixtures and isomers thereof.

In some embodiments the amine may be a diamine, a triamine or a polyamine, having two three or more nitrogen atoms. However preferred amines are monoamines or diamines, especially monoamines. When the amine is a diamine the salt may be a monosalt in which there is only one mole of acid per amine or a disalt in which there are two moles of acid per amine.

Suitable polyamines include polyalkylene polyamines.

Preferred diamines are optionally substituted alkylene diamines, for example ethylene diamines. Thus the amine may be an ethylene diamine of formula $R^1R^2NCH_2CH_2NR^3R^4$ wherein each of each of $R^1$, $R^2$, $R^3$ and $R^4$ is hydrogen or an alkyl group or a hydroxyalkyl group. Each of $R^1$, $R^2$, $R^3$ and $R^4$ may be the same or different. Suitably each $R^1$, $R^2$, $R^3$ and $R^4$ is independently selected from hydrogen and an alkyl or hydroxyalkyl group having 1 to 6 carbon atoms, for example 1 to 4 carbon atoms. Each of $R^1$, $R^2$, $R^3$ and $R^4$ may be independently selected from hydrogen, methyl, ethyl, propyl, butyl, pentyl, hexyl, hydroxymethyl, hydroxyethyl, hydroxypropyl, hydroxybutyl, hydroxypentyl and hydroxyhexyl.

Some especially preferred salts for use herein include the compounds having the following structures.

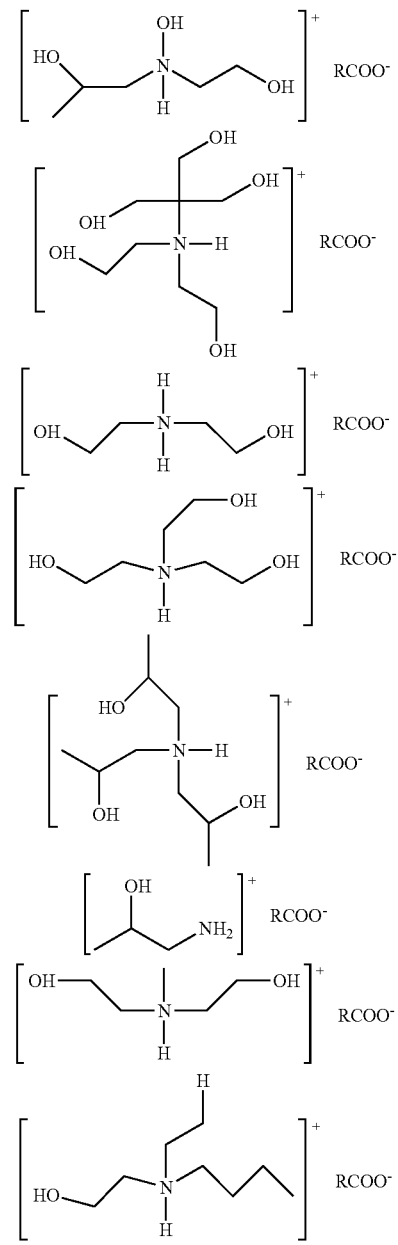

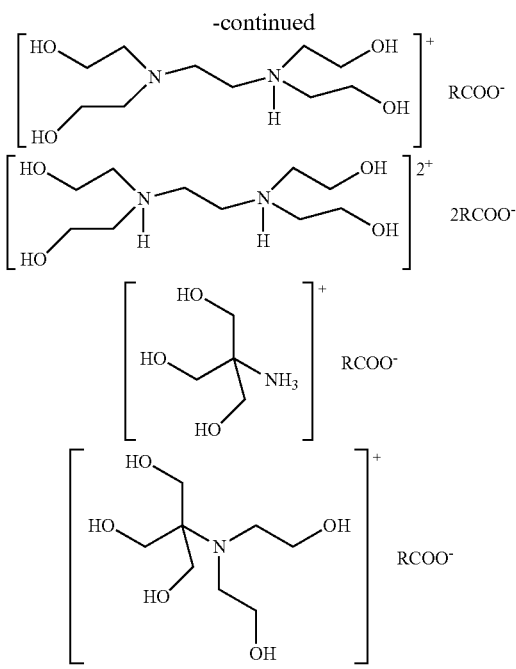

wherein R is an alkyl or alkenyl group having 3 to 9 carbon atoms, preferably pentyl or heptyl.

Preferred amines for use in forming the salts of the present invention are alkanolamines, especially tertiary alkanolamines.

In especially preferred embodiments the composition of the present invention includes a salt of octanoic acid and an amine selected from triethanolamine and diethanolamine, preferably triethanolamine.

Suitably the composition comprises an amine salt of a carboxylic acid wherein the carboxylic acid has 4 to 10 carbon atoms in the amount of at least 0.1 wt %, suitably at least 0.5 wt %, preferably at least 1 wt %, for example at least 1.5 wt %.

The composition may comprise an amine salt of a carboxylic acid wherein the carboxylic acid has 4 to 10 carbon atoms in an amount of up to 100 wt %, preferably up to 50 wt %, preferably up to 30 wt %, suitably up to 20 wt %, preferably up to 10 wt %, more preferably up to 5 wt %, for example up to 4 wt %, up to 3 wt % or up to 2.75 wt %.

In some embodiments the composition comprises from 0.1 to 10 wt % of the amine salt of a carboxylic acid wherein the carboxylic acid has 4 to 10 carbon atoms, preferably from 0.5 to 5 wt %, suitably from 0.5 to 3 wt %.

In some alternative embodiments the composition may comprise much greater concentrations of an amine salt of a carboxylic acid wherein the carboxylic acid has 4 to 10 carbon atoms, for example from 20 to 100 wt %, preferably from 50 to 100 wt %, for example from 70 to 100 wt % or from 90 to 100 wt %.

The composition of the third aspect may comprise a mixture of two or more amine salts of a carboxylic acid wherein the carboxylic acid has 4 to 10 carbon atoms. In such embodiments the above amounts refer to the total amount of all such compounds present in the composition.

In some embodiments the composition of the third aspect comprises a mixture of two or more amine salts of a carboxylic acid wherein the carboxylic acid has 4 to 10 carbon atoms.

The composition of the present invention may be provided in any suitable form. It may be in the form of a gel, paste, cream or wax. It may be in the form of a liquid composition. Such compositions may be in the form of a solution, dispersion or emulsion. It may be provided as a solid composition, for example as a powder or as a bar. In some embodiments a concentrate composition to be diluted prior to use may be provided. In some embodiments the composition of the third aspect may be part of precursor composition to be mixed with one or more further components prior to contact with the material.

The form and nature of the composition of the third aspect will depend on the intended use thereof.

In some embodiments the composition is a laundry detergent composition. In such embodiments the composition suitably comprises one or more further ingredients selected from builders, surfactants, chelating agents, bleaches, optical brighteners, enzymes, fragrances and other such ingredients commonly found in laundry detergent compositions. The composition may be a hand washing laundry detergent composition or an automatic laundry detergent composition.

In especially preferred embodiments the composition is a hair care composition.

Suitably the composition comprises one or more diluents or carriers. Preferred diluents and carriers are cosmetically approved compounds and suitable examples of these will be known to the person skilled in the art. Examples of suitable carriers include organic solvents (eg, hydrocarbon solvents (eg, isododecane), alcohols (eg, ethanol, propanol and butanol), propylene carbonate, benzyl alcohol, aliphatic or aromatic esters (eg, vegetable oils, isopropyl myristate, C12-15 alkyl benzoate), perfluorocarbon solvents, and silicone fluids.

In some embodiments the composition is an aqueous composition. Suitably water is the major solvent present in the composition. In some embodiments water provides for at least 50 wt % of all solvents present in the composition, preferably at least 60 wt %, more preferably at least 70 wt %, suitably at least 80 wt %, for example at least 90 wt % or at least 95 wt %. In some embodiments one or more further water miscible solvents may be present. Examples of suitable water miscible solvents include monohydric and polyhydric alcohols, for example ethanol, glycerol and isopropanol.

In some embodiments the composition of the present invention is not aqueous and the major diluent or carrier is an oleophilic material. In such embodiments the composition may comprise as a major solvent one or more higher fatty alcohols, a mineral oil and/or a vegetable oil.

In some embodiments the composition is substantially aqueous but the salt is dispersed within an oleophilic phase in which it is soluble.

In some embodiments the composition may consist essentially of one or more amine salts of a carboxylic acid wherein the carboxylic acid has 4 to 10 carbon atoms and one or more diluents or carriers. In preferred embodiments the composition comprises one or more further components. Suitable components are those typically used in personal care compositions and are known to the person skilled in the art.

As detailed above the compositions of the present invention may comprise different components depending on the intended use thereof. In some embodiments the composition may be used immediately after dyeing the hair. Alternatively the composition may be used one or more times as a hair treatment composition. In some embodiments it may be provided as a colour-loss prevention composition. Alternatively the composition may be in the form of shampoo, conditioner or hair styling product, for example a serum, wax, mousse, gel or spray or any other hair treatment form that could be used to provide general hair care benefits. Compositions which perform multiple functions, for example combined shampoo and conditioning compositions are also within the scope of the invention.

Suitably the composition comprises one or more additional components selected from surfactants, (including anionic, amphoteric, nonionic and cationic surfactants); conditioning agents (including quaternary ammonium compounds, cationic polymers, silicones, synthetic or natural oils or resins etc), fatty alcohols, electrolytes or other rheology modifiers, opacifying/pearlising agents, scalp benefit agents, fragrances, dyes, UV filters, penetration enhancers (eg, propylene carbonate, benzyl alcohol etc), preservatives, antioxidants, emulsifiers, pH adjusting agents and buffers and styling polymers (eg, polyvinylpyrrolidone etc).

In some embodiments the composition comprises a pH adjusting agent.

Suitable pH adjusting agents for use herein may include lactic acid, sodium hydroxide, sodium phosphate and salts and buffers thereof.

The pH of the composition will depend on the intended use thereof. However in some embodiments the composition has a pH of between 3 and 9, preferably between 3.5 and 8, more preferably between 4 and 7, preferably between 4 and 6. In some other embodiments the composition has a pH of between 8 and 13.

In some preferred embodiments the composition is a hair care composition. Suitable hair care compositions include shampoo compositions, conditioning compositions, hair styling compositions and hair permanent waving, relaxing or permanent straightening compositions, or hair colouring compositions.

Suitable further ingredients and amounts thereof to be used in hair care compositions will be known to the person skilled in the art. The relative ratios of the components and the formulation of such compositions would be within the competence of the skilled person.

Suitably the composition is a substantially aqueous composition, suitably comprising at least 50 wt % water, preferably at least 60 wt %, more preferably at least 70 wt %

Suitably the composition comprises one or more surfactants. For example the composition may comprise from 0.1 to 60 wt % surfactants, preferably from 1 to 30 wt %, suitably from 5 to 25 wt %.

Suitably the composition comprises one or more anionic surfactants. For example the composition may comprise from 0.1 to 60 wt % anionic surfactants, preferably from 1 to 30 wt %, suitably from 5 to 25 wt %.

In some embodiments the composition may comprise a quaternary ammonium salt, suitably in an amount of from 0.1 to 20 wt %, preferably 0.1 to 10 wt %.

In some preferred embodiments the compositions of the present invention comprises less than 5 wt %, preferably less than 1 wt %, suitably less than 0.1 wt % of amine salts of carboxylic acids in which the carboxylic acid has more than 10 carbon atoms.

In some embodiments the composition further comprises an aldehyde. Suitable aldehydes include hydroxy-substituted aldehydes and alpha-substituted aldehydes.

Thus the present invention may provide a hair care composition comprising an amine salt of a carboxylic acid wherein the carboxylic acid has 4 to 10 carbon atoms and an aldehyde which is an alpha-substituted aldehyde and/or a hydroxyaldehyde.

In such embodiments the amine salt is suitably present in an amount of from 0.1 to 50 wt %, preferably 0.1 to 10 wt %, more preferably 0.5 to 5 wt % and the aldehyde is suitably present in an amount of from 0.1 to 50 wt %, preferably 0.1 to 10 wt %, more preferably 0.5 to 5 wt %.

Some preferred aldehydes for use herein have from 3 to 20 carbon atoms, for example 3 to 16 carbon atoms.

Suitable aldehydes for use herein include 2-hydroxydecanal, 2-hydroxydodecanal, 2-hydroxytetradecanal, 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde, 2-(2-hydroxyethoxy)acetaldehyde, 2-chloro octanal, 2-fluoro octanal, 2-bromo octanal, 6-hydroxyhexanal, 3-hydroxypropanal and 4-hydroxy-but-2-enal.

In some embodiments the composition may comprise a first aldehyde having 3 to 9 carbon atoms, preferably 3 to 8 carbon atoms and a second aldehyde having 10 to 18 carbon atoms, preferably 10 to 16 carbon atoms, more preferably 10 to 14 carbon atoms.

Especially preferred aldehydes are α-hydroxy aldehydes. Suitable aldehydes include 2-hydroxypropanal, 2-hydroxyhexanal, 2-hydroxyoctanal and glyceraldehyde.

In some embodiments the composition further comprises a succinimidyl ester. Suitable compounds of this type are described in FR2937543.

Thus the present invention may provide a hair care composition comprising an amine salt of a carboxylic acid wherein the carboxylic acid has 4 to 10 carbon atoms and a succinimidyl ester.

In such embodiments the amine salt is suitably present in an amount of from 0.1 to 50 wt %, preferably 0.1 to 10 wt %, more preferably 0.5 to 5 wt % and the succinimidyl ester is suitably present in an amount of from 0.1 to 50 wt %, preferably 0.1 to 10 wt %, more preferably 0.5 to 5 wt %.

Preferably the succinimidyl ester is a compound of formula (I):

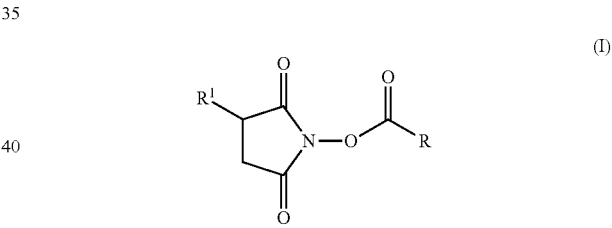

wherein R is an optionally substituted hydrocarbyl group having 5 to 36 carbon atoms; and $R^1$ is hydrogen or a solubilising group.

Preferably R is an optionally substituted alkyl, alkenyl or aryl group having 5 to 20 carbon atoms. More preferably R is selected from phenyl and $CH_3(CH_2)_n$ wherein n is 4 to 10.

Suitably $R^1$ is hydrogen or a sulfonate moiety, preferably hydrogen.

In some embodiments the composition further comprises a chelating agent. Preferred chelating agents are polycarboxylic acid-derived chelating agents.

Thus the present invention may provide a hair care composition comprising an amine salt of a carboxylic acid wherein the carboxylic acid has 4 to 10 carbon atoms and a poly carboxylic acid-derived chelating agent.

In such embodiments the amine salt is suitably present in an amount of from 0.1 to 50 wt %, preferably 0.1 to 10 wt %, more preferably 0.5 to 5 wt % and the chelating agent is suitably present in an amount of from 0.1 to 50 wt %, preferably 0.1 to 10 wt %, more preferably 0.5 to 5 wt %.

Suitably the chelating agent is selected from glutamic acid N,N-diacetic acid (GLDA), diethylene triamine pentaacetic acid (DTPA), imido disuccinic acid (IDS), L-aspartic acid diacetic acid (ASDA), ethylene diamine tetraacetic acid (EDTA), ethylene diamine disuccinic acid (EDDS), hydroxyethyl ethylenediaminetriacetic acid (HEDTA), citric acid and mixtures thereof.

In some preferred embodiments the chelating agent is selected from DTPA, GLDA, IDS and mixtures thereof. In some especially preferred embodiments the chelating agent is selected from DTPA, GLDA and mixtures thereof.

In some embodiments the composition further comprises an aldehyde that is an alpha-substituted aldehyde and/or a hydroxy aldehyde, and a polycarboxylic acid derived chelating agent.

In some embodiments the composition further comprises an aldehyde that is an alpha-substituted aldehyde and/or a hydroxy aldehyde, and a succinimidyl ester.

In some embodiments the composition further comprises a succinimidyl ester and a polycarboxylic acid derived chelating agent.

In some embodiments the composition further comprises an aldehyde that is an alpha-substituted aldehyde and/or a hydroxy aldehyde, a succinimidyl ester and a polycarboxylic acid derived chelating agent.

In some embodiments the composition may further comprise a crosslinking agent comprising two or more reactive moieties and a linker. Compounds of this type are described for example in US2015/034117 and US2015/0034119.

In some embodiments the reactive moieties are activated carboxylic acid or sulfonic acid derivatives and the linkers are polyamino compounds which may form salts or covalent bonds with the reactive moieties.

In some embodiments the reactive moieties are maleic acid derivatives and the linker has two or more amino groups linked by alkylene or oxyalkylene chains. The crosslinking agent may be a maleimide or a maleic acid amine salt.

In some embodiments the reactive moieties are maleic acid ions and the linker comprises quaternary ammonium ions linked by alkylene or oxyalkylene chains.

Some preferred crosslinking agents have the following structures:

anionic surfactants, preferably 1 to 50 wt %, more preferably 5 to 30 wt %, for example 8 to 20 wt % or 8 to 12 wt %; optionally from 0.1 to 30 wt % of amphoteric surfactants, preferably 1 to 15 wt %, for example 2 to 12 wt %; and optionally 0.1 to 40 wt % of non-ionic surfactants, preferably 0.5 to 30 wt %, for example 1 to 15 wt % or 2 to 12 wt %.

Shampoo compositions of the present invention may comprise one or more ingredients selected from anionic surfactants (eg, sodium laureth sulfate, sodium lauroyl methyl isethionate, sodium cocoyl methyl isethionate, sodium alpha-olefin sulfonate, sodium lauryl sulfoacetate, sodium monoalkyl phosphates, sodium dialkyl phosphates and sodium cocoyl methyl taurate, amphoteric surfactants (eg, cocamidopropyl betaine sodium lauroamphoacetate, cocamidopropylhydroxy sultaine and disodium cocoamphodiacetate), foam boosters (eg, cocamide DEA, cocamide MEA, cocamide MIPA laureth-3), fatty alkyl alcohols (eg, cetyl alcohol, stearyl alcohol and behenyl alcohol) nonionic surfactants (eg, alkylpolyglucosides and alkyl ether ethoxylates), cationic polymers (eg, guar hydroxypropyl trimonium chloride, polyquaternium-10), silicones (eg, polydimethylsiloxanes such as dimethicone and dimethiconol), rheology modifiers (eg, carbomer, PEG-150 distearate and xanthan gum), synthetic or natural oils or resins (eg, mineral oil or vegetable oils), anti-dandruff agents (eg, piroctone olamine, zinc pyrithione and salicylic acid), styling agents (eg, polyisobutylene and polyvinyl pyrollidone/vinyl acetate copolymer), moisturising agents (eg, panthenol and glycerol), non-polymeric conditioning agents (eg, quaternary ammonium compounds such as behentrimonium chloride and stearalkonium chloride), opacifying/pearlising agents (eg, styrene/acrylates copolymer and ethylene glycol distearate), scalp benefit agents, fragrance, colouring agents, hair dyes, sunscreens, UV filters, preservatives, penetration enhancers

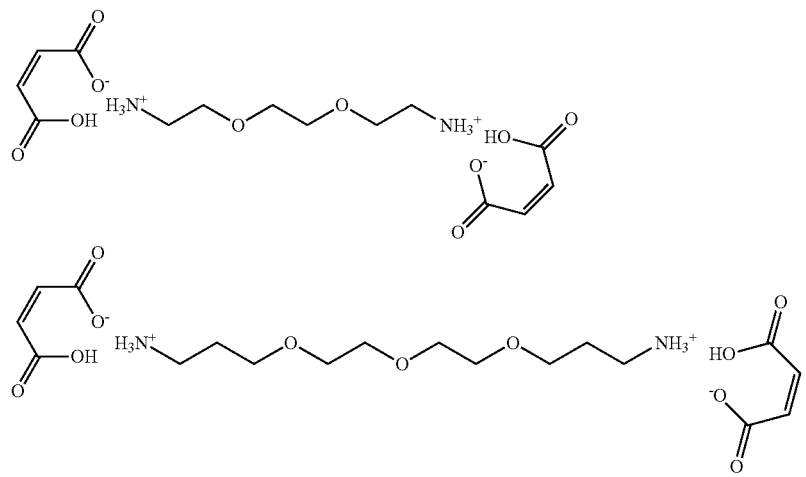

The crosslinking agent comprising two or more reactive moieties and a linker may be present in an amount of from 0.1 to 30 wt %, preferably 0.1 to 10 wt %, suitably 0.5 to 5 wt %.

In some embodiments the composition of the third aspect of the present invention is a shampoo composition.

Suitable shampoo compositions of the present invention may typically comprise 0.5 to 60 wt % of one or more (eg, propylene carbonate, benzyl alcohol etc) and diluents and carriers as defined herein.

Some preferred shampoo compositions of the present invention include 0.5 to 60 wt % of one or more anionic surfactants (for example, sodium laureth sulfate, sodium lauroyl methyl isethionate, sodium cocoyl isethionate, sodium alpha-olefin sulfonate, sodium lauryl sulfoacetate, sodium monoalkyl phosphates and sodium dialkyl phosphates); and 0 to 30 wt % of amphoteric surfactants (for example, cocamidopropyl betaine, sodium lauroamphoacetate and cocamidopropylhydroxy sultaine).

In some embodiments the composition of the third aspect of the present invention is a conditioning composition.

Suitable conditioning compositions of the present invention may typically comprise 0.1 to 20 wt % of one or more cationic surfactants, preferably 0.5 to 8 wt %, more preferably 1 to 4 wt %; and 0.1 to 20 wt % of one or more fatty alkyl alcohols, preferably 0.5 to 8 wt %, more preferably 1 to 4 wt %; and optionally 0.1 to 20 wt % of one or more non-ionic surfactants, preferably 0.5 to 8 wt %, more preferably 1 to 4 wt %; and optionally 0.1 to 20 wt % of one or more cationic polymers, preferably 0.5 to 8 wt %, more preferably 1 to 4 wt %.

Conditioning compositions of the present invention including rinse-off and leave-on conditioners (including 'hair masks') and hair shine or appearance enhancing products, anti-frizz treatment serums and other treatments, either leave-in or rinse-off, designed to be applied to the hair immediately after colouring or any time thereafter, and hair-tonics. Such compositions may comprise one or more further ingredients selected from: cationic surfactants including mono- and di-fatty alkyl tertiary amines and quaternary ammonium compounds (eg, mono- and di-fatty alkyl quaternary ammonium compounds, such as cetrimonium chloride, steartrimonium chloride and behentrimonium chloride), fatty alkyl alcohols (eg, cetyl alcohol, stearyl alcohol and behenyl alcohol), nonionic surfactants (eg, alkylpolyglucosides and alkyl ether ethoxylates, eg, ceteareth-20), cationic polymers (eg, guar hydroxypropyl trimonium chloride, polyquaternium-10), silicones (eg, polydimethylsiloxanes such as dimethicone and dimethiconol), rheology modifiers (eg, hydroxyethyl cellulose and polyquaternium-37), moisturising agents (eg, panthenol and glycerol), non-polymeric conditioning agents (eg, quaternary ammonium compounds such as behentrimonium chloride and stearalkonium chloride), scalp benefit agents, fragrance, colouring agents, hair dyes, sunscreens, UV filters preservatives, penetration enhancers (eg, propylene carbonate, benzyl alcohol, etc), and diluents and carriers as defined herein.

Some preferred conditioning compositions of the present invention include 0.1 to 20 wt % of cationic surfactants (for example mono- and di-fatty alkyl quaternary ammonium compounds, mono- and di-fatty alkyl tertiary amines), 0.1 to 20 wt % of fatty alkyl alcohols; and 0.1 to 20 wt % of non-ionic surfactants (for example ceteareth-20).

In some embodiments the composition of the third aspect of the invention is a hair styling composition.

Suitable hair styling compositions of the present invention may typically comprise from 0.1 to 40 wt % of one or more hair styling polymers, preferably from 0.1 to 30 wt %, more preferably from 0.5 to 10 wt %.

Hair styling compositions of the present invention (including gels, mousses with and without propellant, hair sprays with and without propellant, hair pomades, hair waxes, hair creams, hair brilliantines and compositions designed to be used in conjunction with heated styling appliances such as blow dryers, curling tongs, straightening irons, hot air hoods (as used for example in hair salons)) may comprise one or more further ingredients selected from: hair styling polymers (eg, polyvinylpyrrolidone, polyvinylpyrrolidone/vinyl acetate copolymers, octylacrylamide/acrylates/butylaminoethyl methacrylate copolymer, methyl vinyl ether/maleic anhydride copolymers and polyethylene waxes), rheology modifiers (eg, carbomers, acrylates copolymers, hydroxethylcellulose, xanthan gum and polyquaternium-37), aminomethyl propanol, fatty alkyl alcohols (eg, cetyl alcohol, stearyl alcohol and behenyl alcohol), ethanol, propyl alcohol, isopropyl alcohol, petrolatum, mineral oil, ozokerite, beeswax, carnauba wax, silicones (eg, polydimethylsiloxanes such as dimethicone and dimethiconol), polyethylene glycols, anionic surfactants (eg, sodium laureth sulfate and sodium lauroyl methyl isethionate), amphoteric surfactants (eg, cocamidopropyl betaine and disodium cocoamphodiacetate), nonionic surfactants (eg, alkylpolyglucosides and alkyl ether ethoxylates), cationic polymers (eg, guar hydroxypropyl trimonium chloride, polyquaternium-10), silicones (eg, polydimethylsiloxanes such as dimethicone and dimethiconol), moisturising agents (eg, panthenol and glycerol), non-polymeric conditioning agents (eg, quaternary ammonium compounds such as behentrimonium chloride and stearalkonium chloride), scalp benefit agents, fragrance, colouring agents, hair dyes, sunscreens, UV filters, preservatives, penetration enhancers (eg, propylene carbonate, benzyl alcohol, etc), and diluents and carriers as defined herein.

Some preferred hair styling compositions of the present invention include 0.1 to 40 wt % of one or more hair styling polymers/resins (for example polyvinylpyrrolidone, polyvinylpyrrolidone/vinyl acetate copolymers, octylacrylamide/acrylates/butylaminoethyl methacrylate copolymer, methyl vinyl ether/maleic anhydride copolymers and polyethylene waxes).

Those skilled in the art will appreciate that it is possible to confer one or more attributes of hair conditioning, shine etc, and hair styling to the hair from a single product containing the appropriate ingredients thus, compositions having such combinations of hair benefit effects are also covered in the invention.

In some embodiments the composition of the third aspect is a hair permanent waving composition.

Suitable hair permanent waving compositions of the present invention may typically comprise 0.1 to 20 wt % of one or more reducing agents, preferably from 0.5 to 15 wt %, more preferably 3 to 12 wt %.

Some preferred hair permanent waving compositions of the present invention include 0.5 to 15 wt % of one or more reducing agents (for example as thioglycolic acid, ammonium thioglycolate, thiolactic acid, cysteamine, cysteine, glycerol monothioglycolate, sodium sulfite/bisulfite); alkalising agents (for example ammonia, monoethanolamine) in an amount sufficient to adjust the pH of the reducing component to between pH 8-13. Hair permanent waving compositions are typically provided in a package with a second composition comprising 0.5 to 10 wt % of one or more oxidising agents (for example hydrogen peroxide, sodium bromate, sodium percarbonate and sodium perborate) which are applied after the reducing agent composition has been applied, allowed to process and then rinsed off.

In some embodiments the composition of the third aspect of the present invention is a hair relaxing composition.

Hair relaxing compositions of the present invention may include one or more ingredients selected from sodium hydroxide, lithium hydroxide, potassium hydroxide, calcium hydroxide and guanidine carbonate. These components are suitably present in an amount of from 0.5 to 5 wt %.

Other types of permanent straightening compositions may include one or more ingredients selected from formaldehyde, glycoxylic acid, glutaraldehyde and glyoxyloyl carbocysteine. These components are suitably present in an amount of from 0.1 to 10 wt %.

The hair permanent waving, relaxing and permanent straightening compositions mentioned above may further include one or more additional ingredients selected from anionic surfactants (eg, sodium laureth sulfate and sodium lauroyl methyl isethionate), amphoteric surfactants (eg, cocamidopropyl betaine and disodium cocoamphodiacetate), quaternary ammonium compounds (eg, cetrimonium chloride, steartrimonium chloride and behentrimonium chloride), fatty alkyl alcohols (eg, cetyl alcohol, stearyl alcohol and behenyl alcohol), nonionic surfactants (eg, alkylpolyglucosides and alkyl ether ethoxylates), cationic polymers (eg, guar hydroxypropyl trimonium chloride, polyquatemium-10), silicones (eg, polydimethylsiloxanes such as dimethicone and dimethiconol), opacifying agents (eg, styrene acrylates copolymer), rheology modifiers (eg, hydroxyethyl cellulose and xanthan gum), moisturising agents (eg, panthenol and glycerol), non-polymeric conditioning agents (eg, quaternary ammonium compounds such as behentrimonium chloride and stearalkonium chloride), fragrance, sunscreens, UV filters, colouring agents and diluents and carriers as defined herein.

In some embodiments the composition of the third aspect of the present invention is a hair colouring composition.

Hair colouring compositions may include a dye compound and/or may include a dye precursor compound which forms an active dye in the hair in situ following admixture with an oxidising composition.

Oxidative hair colouring compositions of the present invention may include one or more intermediates, for example p-phenylenediamine, N,N-bis(2-hydroxyethyl)-p-phenylenediamine, p-toluenediamine, p-aminophenol phenyl methyl pyrazolone, m-phenylenediamine, resorcinol, 1-naphthol, 1-hydroxyethyl 4,5-diamino pyrazole and m-aminophenol. These intermediates can be present in any combination and ratios at a total intermediate concentration of from 0.01 to 15% depending upon the desired shade. Such compositions typically further include one or more alkalising agents, for example ammonia, ammonium hydroxide, sodium hydroxide and monoethanolamine. Developer compositions for oxidative dyeing include an oxidising agent, for example hydrogen peroxide, sodium bromate, sodium percarbonate or sodium perborate. These are typically present in an amount of from 0.1 to 30 wt %.

Direct-dye colour compositions of the present invention may include one of more direct dyes for example from the classes of nitrophenylenediamines (eg, 4-nitro-o-phenylenediamine etc), nitroaminophenols (eg, 2-amino-4-nitrophenol etc), and aminoanthraquinones (eg, Disperse Red 11 etc). These are typically present in an amount of 0.1 to 20 wt %, depending on the desired shade.

In some preferred embodiments the composition of the present invention is not a hair colouring composition. Preferably the composition comprises less than 0.1 wt %, preferably less than 0.01 wt % of dye compounds and/or dye precursor compounds. Preferably the composition does not comprise dye compounds and/or dye precursor compounds. Compounds which provide colour to the composition such as pigments and pearlescent agents may be present but suitably the composition does not include any compounds which may be used to dye hair.

In the method of the first aspect the material is contacted with a composition comprising an amine salt of a carboxylic acid wherein the carboxylic acid has 4 to 10 carbon atoms.

The material, preferably hair, may be wet or dry when contacted with the composition.

Suitably the composition is applied to the material and spread across the surface of the material. In preferred embodiments in which the material is hair the composition may be rubbed into the hair in the manner of a shampoo and/or it may be combed through the hair.

The composition of the present invention may be left on the material or it may be removed from the material. Suitably it may be rinsed using warm water.

In some embodiments the composition may be contacted with the material, spread throughout and then immediately removed.

Suitably the composition may be removed from the material by rinsing, preferably by using water.

In some embodiments the composition may be washed from the material by washing with a detergent composition.

In some embodiments the composition may be mechanically removed from the material, for example by brushing.

In some embodiments the composition may be left on the material and not removed until the material is washed during a normal cycle.

In some embodiments in which the material is hair, the composition may be applied to the hair, spread throughout and rubbed into the hair, and then rinsed with water, in the manner of a shampoo.

In some embodiments in which the material is hair, the composition may be applied to the hair, spread throughout the hair (optionally with combing), left on the hair for a short period and then rinsed from the hair with water, in the manner of a conditioner.

In some embodiments in which the material is hair, the composition may be contacted with the hair and left on the hair in the manner of a styling product. The composition may be sprayed throughout the hair, rubbed throughout the hair, combed throughout the hair or otherwise spread through the hair in a manner known to those skilled in the art.

In embodiments in which the composition is left on the hair, it suitably remains on the hair until the hair is next washed, although some of the composition may be brushed out or rubbed away during normal activity.

In the method of the present invention the composition is suitably contacted with the material, preferably hair, at ambient temperature. In some embodiments the composition may be contacted with the material at a temperature greater than the ambient temperature.

In some embodiments the composition may be contacted with the hair and the hair carrying the compositions is then heated and/or manipulated and/or dried. Thus the hair may be dried using a hairdryer or straightened after the composition is applied.

The methods of the first and second aspect of the present invention may involve heating the hair. Such a heating step may involve commonly used heating techniques such as blow drying, or using tongs, straighteners or hoods etc.

The present invention provides a method of combating colour loss from a dyed material, preferably from dyed hair. By combating colour loss we mean to include reducing the loss of colour from a dyed material and/or preventing or inhibiting the loss of colour from a dyed material, for example dyed hair.

There are a number of ways which colour loss can be measured. For example colour intensity can be measured immediately after dyeing and then after a period of time or after a number of washes. Any colour loss from a material treated according to the present invention can be compared with a control sample which is dyed and subsequently treated in an identical manner except for the use of the amine salt of a carboxylic acid wherein the carboxylic acid has 4 to 10 carbon atoms according to the invention.

Skilled experienced professionals are able to judge colour tone and intensity by sight and thus colour loss can be assessed by the naked eye. However in many cases a suitable device is used. Such devices and the operation thereof are known to the person skilled in the art and include for example chromameters or colourimeters.

A standard method of defining a colour difference is to provide a dE (or ΔE or delta E) measurement. This uses a formula to calculate colour difference based CIELAB measurements.

One suitable method of determining colour loss is to measure the reflectance of light at a particular wavelength. The difference in reflectance after time, washing or other treatment can be compared with a control. For example the reflectance of light at 457 nm could be measured (R457).

One suitable method is described in example 2.

Preferably the method of the present invention reduces colour loss by at least 10%, preferably at least 20%, more preferably at least 30%, for example at least 40%.

In some embodiments, the method of the present invention may reduce colour loss by more than 50%, preferably by more than 60%, more preferably by more than 70%, for example by more than 80% or more than 90%.

By a reduction of at least 10% we mean that if a material is treated according to the method of the present invention the colour loss is at least 10% less than if a material is treated with an equivalent method in which the salt of an amine and a carboxylic acid having 4 to 10 carbon atoms is not included. For example in the case of a shampoo composition, washing the hair with a shampoo comprising an amine salt of a carboxylic acid wherein the carboxylic acid has 4 to 10 carbon atoms provides a 10% reduction in colour loss compared with washing with a shampoo which is otherwise identical but does not contain the amine salt of a carboxylic acid wherein the carboxylic acid has 4 to 10 carbon atoms.

Suitably the method of the present invention provides a reduction in colour loss of at least 10%, preferably at least 20%, suitably at least 30%, compared with a control when measured according to the method of example 2. In this regard it should be noted that the control provides a colour loss of 100%. Thus if a colour loss of 90% is observed, this represents a reduction in colour loss of 10%.

The present invention may involve contacting the material with a composition comprising an amine salt of a carboxylic acid wherein the carboxylic acid has 4 to 10 carbon atoms once or more than once.

The invention may be used on a regular basis, for example every time hair (or another material) is washed. Alternatively the invention may be used periodically on a less frequent basis, for example, every week or every month.

It has been surprisingly found that the method of the present invention can significantly reduce the loss of colour from dyed hair.

The present invention may provide reduced colour loss following a number of washes. For example in embodiments in which the invention relates to a colouring composition the inclusion of an amine salt of a carboxylic acid wherein the carboxylic acid has 4 to 10 carbon atoms at some stage in the dyeing process may provide improved wash fastness and/or reduced colour fade over time.

Preferably dyeing the hair according to the method of the second aspect provides improved wash fastness. Suitably hair dyed according to the method of the second aspect has colour loss of at least 10% less after three washes compared with hair dyed by an equivalent method excluding the amine salt of a carboxylic acid wherein the carboxylic acid has 4 to 10 carbon atoms, preferably at least 30%, more preferably at least 50%.

According to a fourth aspect of the present invention there is provided the use of an amine salt of a carboxylic acid wherein the carboxylic acid has 4 to 10 carbon atoms to combat colour loss from dyed hair.

According to an fifth aspect of the present invention there is provided a packaged hair colouring product comprising one or more compositions wherein the one or more compositions together comprise at least one dye compound and/or one dye precursor compound and an amine salt of a carboxylic acid wherein the carboxylic acid has 4 to 10 carbon atoms.

Preferred features of the product of the fifth aspect are as described in relation to the first, second, third and fourth aspects and the product is suitable for use in the colouring method of the second aspect.

In some embodiments the product of the fifth aspect may be a product for oxidative dyeing of the hair comprising a first composition comprising one or more dye precursor compounds and a second oxidising composition comprising one or more oxidising agents. The amine salt of a carboxylic acid wherein the carboxylic acid has 4 to 10 carbon atoms may be included in the composition comprising the one or more dye precursor compounds and/or in the composition comprising the oxidising agent. However in preferred embodiments it is provided as a separate third composition. This third composition can be applied to the hair before, during or after treatment with the first and/or second compositions. Alternatively it may be admixed with the first or second composition prior to contact with the hair.

The invention will now be further defined with reference to the following non-limiting examples.

EXAMPLE 1

Wool swatches were dyed with an oxidative red dye formed as follows:

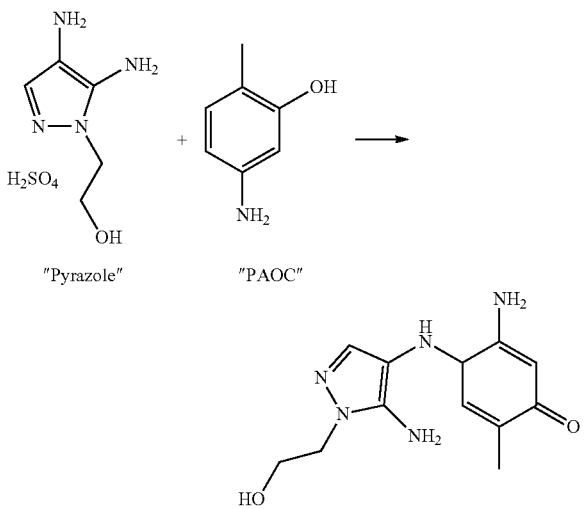

The dyed swatches were immersed in an aqueous solution comprising the test compounds listed in table 1 at 2 wt % (except compound 5) and 0.1 wt % SLES buffered to pH 5.5 with sodium acetate buffer for 30 minutes at 40° C. The swatches were then rinsed in water for 2 minutes and then dried. A 30 minute treatment represents a relatively severe test, equivalent to multiple "regular" washes.

A visual assessment was made of the cloth and this was rated on a scale of 1-5, as follows:
1 Colour significantly more intense than control and close to original colour
2 Colour visibly more intense than control
3 Colour not visibly more intense than control
4 Colour visibly less intense than control
5 Colour significantly less intense than control or colour hue change (eg, blue) or cloth greasy or spotted (reasons recorded)

For cloths visually assessed as more intense than the control (Score 1 or 2), then the actual reading of the colour intensity was measured using standard reflectometry and compared with a deionised water control (containing 0.1 wt % SLES). 100% is the amount of dye removed by the control and a number <100% shows less dye removal than the control and 0% is the colour of the original cloth. In this case the difference in reflectance of light having a wavelength of 457 nm was measured.

Table 1 details the compounds tested and the results obtained. Compounds 1 to 5 are of the invention. Compounds 6 to 9 are comparative examples.

TABLE 1

| | Compound | | | |
|---|---|---|---|---|
| | Acid | Amine | Score | Result |
| 1 | hexanoic acid | diethanolamine | 2 | |
| 2 | octanoic acid | diethanolamine | 2 | 16% |
| 3 | octanoic acid | triethanolamine | 2 | 43% |
| 4 | octanoic acid | Bis tris | 2 | 55% |
| 5 | octanoic acid | N,N,N',N'-Tetrakis(2-hydroxyethyl)ethylenediamine | 1 | 20% |
| 6 | formic acid | diethanolamine | 3 | |
| 7 | acetic acid | diethanolamine | 3 | |

EXAMPLE 2

The wash fastness of the dyeings according to the invention was assessed according to the following method.

Wool swatch samples were initially treated as in example 2. They were then treated with a deionized water composition comprising 0.1% SLES for wetting for 15 minutes, rinsed and dried. The reflectance at 457 nm (R457) was measured. A further two washing steps with deionized water comprising 0.1% SLES were carried out for 30 minutes each.

The results in table 2 are the absolute values of ΔR457 wherein ΔR457 is the difference in reflectance at 457 nm between the initially dyed wool swatches and the swatches that have been treated as detailed in the table.

TABLE 2

| Composition | Salt | 30 min treatment with salt | Wash 15 min | Wash 45 min (total) | Wash 75 min (total) | % colour loss compared to control |
|---|---|---|---|---|---|---|
| 1 | diethanolamine salt of octanoic acid | −0.6 | 1.2 | 5.3 | 7.6 | 38 |
| 2 | 0.1% SLES (control) | 4.55 | 7.9 | 14.9 | 19.8 | 100 |

The results in table 2 and figure 1 clearly show that the present invention provides a benefit in terms of reducing subsequent leaching of dye relative to the control.

EXAMPLE 3

The effect of multiple treatments with an amine salt of a carboxylic acid wherein the carboxylic acid has 4 to 10 carbon atoms was carried out by repeatedly contacting wool swatches with the amine salt as generally described in example 1 for periods of 30 or 15 minutes. After each treatment the swatches were then rinsed in water for 2 minutes and then dried.

The results in table 2 are the absolute values of ΔR457 wherein ΔR457 is the difference in reflectance at 457 nm between the initially dyed wool swatches and the swatches that have been treated as detailed in the table.

TABLE 3

| | Initial 30 minute treatment | 15 minute | 15 minute | 15 minute |
|---|---|---|---|---|
| Octanoic acid diethanolamine salt | 1.2 | 2.2 | 3.1 | 3.8 |
| 0.1% SLES (control) | 5.2 | 8.1 | 12.9 | 16.9 |

EXAMPLE 4

A study of the use of shampoo compositions comprising the triethanolamine salt of octanoic acid to achieve wash fastness was carried out according to the following method.

Wool swatch samples were treated as in example 2 using 3 wt % and 4 wt % solutions of the triethanolamine salt of octanoic acid or deionised water control and 10% of a basic shampoo formula (12.5 wt % SLES, 2.5 wt % CAPB in water). The results in Table 4 are the absolute values of ΔR457 wherein ΔR457 is the difference in reflectance at 457 nm between the initially dyed wool swatches and the swatches that have been treated with the inventive composition or the control.

TABLE 4

| Composition | ΔR457 |
|---|---|
| Shampoo + 3 wt % octanoic acid triethanolamine salt | 0.9 |
| Shampoo + 4 wt % octanoic acid triethanolamine salt | 2.0 |
| Shampoo control | 8.1 |

The invention claimed is:

1. A method of combatting colour loss from a dyed keratinous material, the method comprising contacting the material with a composition comprising up to 4 wt % of an amine salt of a carboxylic acid of formula RCOOH wherein R is an unsubstituted alkyl group having 3 to 9 carbon atoms, and wherein the amine moiety is selected from the group consisting of diethanolamine and triethanolamine.

2. The method according to claim 1 wherein the material is human hair or animal hair.

3. The method according to claim 2 wherein the material is growing human hair or animal hair.

4. The method according to claim 1 wherein the composition comprising the amine salt of a carboxylic acid of formula RCOOH wherein R is an unsubstituted alkyl group having 3 to 9 carbon atoms is selected from the group consisting of a shampoo composition, a conditioning composition, a hair styling composition, a hair permanent waving composition, a hair relaxing composition, a hair permanent straightening composition and a hair colouring composition.

5. The method according to claim 1 wherein the composition comprising the amine salt of a carboxylic acid of formula RCOOH wherein R is an unsubstituted alkyl group having 3 to 9 carbon atoms further comprises 1 to 30 wt % of one or more surfactants.

6. The method according to claim 1 wherein the carboxylic acid has 6 to 8 carbon atoms.

7. The method according to claim 1 wherein the amine salt of a carboxylic acid of formula RCOOH wherein R is an unsubstituted alkyl group having 3 to 9 carbon atoms is a salt of n-hexanoic acid or n-octanoic acid.

8. The method according to claim 1 wherein the amine salt of a carboxylic acid of formula RCOOH wherein R is an unsubstituted alkyl group having 3 to 9 carbon atoms is selected from the group consisting of triethanolamine salt of hexanoic acid, diethanolamine salt of the hexanoic acid, diethanolamine salt of octanoic acid and triethanolamine salt of octanoic acid.

9. The method according to claim 1 wherein the composition comprising the amine salt further comprises an aldehyde which is an alpha-substituted aldehyde and/or a hydroxyaldehyde.

10. The method according to claim 1 wherein the composition comprising the amine salt further comprises a polycarboxylic acid derived chelating agent.

11. The method according to claim 1 wherein the composition comprising the amine salt further comprises a succinimidyl ester.

12. The method according to claim 1 wherein the composition comprising the amine salt further comprises a crosslinking agent comprising two or more maleic acid derived reactive moieties and a linker having two or more amino groups.

13. The method according to claim 1 which reduces colour loss by at least 20%.

14. The method according to claim 1 wherein the dyed keratinous material is a textile material.

15. The method according to claim 1 which combats colour loss resulting from washing a dyed textile material in a laundry washing process.

* * * * *